United States Patent [19]
Buckman et al.

[11] 3,973,034
[45] Aug. 3, 1976

[54] CERTAIN STABILIZED DITHIOCARBOMATE PESTICIDAL COMPOSITIONS AND METHODS OF USING SAME

[75] Inventors: John D. Buckman; John D. Pera, both of Memphis, Tenn.

[73] Assignee: Buckman Laboratories, Inc., Memphis, Tenn.

[22] Filed: May 28, 1974

[21] Appl. No.: 473,618

Related U.S. Application Data

[63] Continuation-in-part of Ser. No. 246,961, April 24, 1972, Pat. No. 3,856,851.

[52] U.S. Cl. .................................... 424/286; 71/67; 210/64; 162/161; 260/45.9 NC

[51] Int. Cl.$^2$ ........................ A01N 9/12; A01N 9/20
[58] Field of Search .................... 260/513.5; 424/286

[56] References Cited
UNITED STATES PATENTS

| | | | |
|---|---|---|---|
| 2,791,605 | 5/1957 | Dorman et al. | 424/286 |
| 3,050,552 | 8/1962 | Nemec et al. | 424/286 |
| 3,577,547 | 5/1971 | Pelissier et al. | 424/286 |

*Primary Examiner*—V. D. Turner
*Attorney, Agent, or Firm*—Floyd Trimble

[57] ABSTRACT

Pesticidal compositions comprised of alkali-metal salts of hydroxymethyldithiocarbamic acids in aqueous media are stabilized by addition of alkaline material thereto.

15 Claims, No Drawings

CERTAIN STABILIZED DITHIOCARBOMATE PESTICIDAL COMPOSITIONS AND METHODS OF USING SAME

RELATED APPLICATION DATA

This application is a continuation-in-part of copending application Ser. No. 246,961 filed Apr. 24, 1972 for Novel Metal Salts of Dithiocarbamic Acids, now U.S. Pat. No. 3,856,851, Dec. 24, 1974.

BACKGROUND OF THE INVENTION

1. Field of the Invention

This invention relates to novel compositions and the use of the same as bactericides, fungicides, algicides, nematocides, and soil fumigants in industry and agriculture. More particularly, the present invention relates to compositions comprising alkali-metal salts of dithiocarbamic acids and the pesticidal use thereof.

2. Description of the Prior Art

A great number of dithiocarbamic acid salts have been described in the chemical literature as commercial, industrial, and agricultural microbicides and nematocides. Fungicidal dithiocarbamic acid derivatives are described in U.S. Pat. No. 3,084,095. Salts of dithiocarbamic acids are also described in U.S. Pat. Nos. 2,589,209 and 2,609,389. In our copending U.S. application Ser. No. 246,961, of which this application is a continuation-in-part, we described compounds characterized as the reaction products of (1) $C_1$ to $C_3$ alkylaldehydes, (2) ammonia, primary $C_1$ to $C_5$ monoalkylamines, or primary $C_2$ to $C_4$ alkylenediamines, and (3) alkali-metal or alkaline-earth-metal salts of dithiocarbamic acid, of N-$C_1$ to $C_5$ alkyldithiocarbamic acid, or an N,N'-$C_2$ to $C_4$ alkylenebisdithiocarbamic acid. These compounds were shown to have greater effectiveness against microorganisms and nematodes than did the dithiocarbamic acid salts themselves. Nevertheless, there has been a continuing need for pesticidal compositions of enhanced activity and long term stability.

SUMMARY OF THE INVENTION

According to the present invention, pesticidal compositions comprising aqueous solutions or aqueous slurries of alkali-metal salts of N-hydroxymethyl-N-alkyldithiocarbamate or N,N'-bishydroxymethyl-N,N'-alkylenebisdithiocarbamate are provided. The compositions are stabilized against precipitation in storage by addition of an alkaline material thereto. Also, the effectiveness of the compositions is enhanced by addition of the proper amount of alkaline material.

The compositions of our invention are useful for slime control in pulp and paper mills, as microbicides and algicides for the treatment of fresh water used in industrial processes, and as microbicides and algicides in cooling towers. The compositions of this invention are useful agricultural bactericides, fungicides, nematocides, and soil fumigants. In addition, the products are stable in alkaline systems and are, therefore, useful as preservatives for adhesives; caulking, grouting, spackling compounds, and joint cements; detergents; floor wax emulsions and floor polishes; inks; latex emulsions; laundry starch; cutting fluid emulsions; latex paints; coatings, finishes and printing colors based on starch and latex for pulp and paper; and spinning emulsions, finishing solutions and printing pastes used in the textile industry. These products are also effective against sulfate-reducing and iron bacteria and are therefore useful for secondary and tertiary recovery operations in the petroleum industry.

As to the amount of the alkali-metal dithiocarbamates to be added to the aqueous systems, a suitable quantity varies from about 0.01 to 10,000 parts per million parts of water. It will be understood, however, that larger quantities may be used with no detrimental effect, but such larger quantities increase the cost of operation with limited material benefit. When the products of this invention are used as nematocides, suitable quantities vary from about 0.1 to 20.0 pounds per acre. When used as soil fumigants, suitable quantities vary from 10 to 300 pounds per acre. As mentioned above, larger quantities may be used with no detrimental effect.

It is an object of this invention to provide novel pesticidal compositions. It is a further object to provide such compositions having enhanced activity and stability against precipitation in storage.

DETAILED DESCRIPTION OF THE PREFERRED EMBODIMENTS

The pesticidal compositions of this invention comprise an aqueous solution or an aqueous slurry of a compound having either the formula

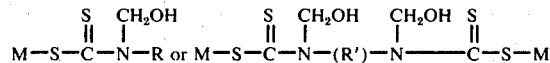

wherein M is an alkali metal, R is an alkyl group having from one to five carbon atoms, and R' is an alkylene group having from two to four carbon atoms.

These compounds may be prepared by reaction, in an aqueous solution, of an alkali-metal salt of an N-$C_1$ to $C_5$ alkyldithiocarbamate or an alkali-metal salt of an N,N'-$C_2$ to $C_4$ alkylenebisdithiocarbamate with formaldehyde. The appropriate dithiocarbamates must contain a free hydrogen atom on each nitrogen of the dithiocarbamate group or groups. The resulting compounds have a hydroxymethyl group in place of the free hydrogen on the dithiocarbamate group or groups.

The compounds produced by reacting the starting dithiocarbamate with formaldehyde are initially soluble in water, but upon standing precipitates of unknown composition are formed. These precipitates are not readily redissolved and are believed to be a polymeric material.

We have found that these precipitates can be prevented by stabilization of the aqueous medium containing the reaction product of the dithiocarbamates and formaldehyde. This stabilization is effected by addition of an alkaline material to the aqueous medium. In addition to stabilizing the compositions, it has been found that the pesticidal activity of the compositions is enhanced by addition of an appropriate amount of alkaline material.

Compounds having the formula

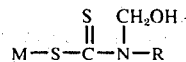

where M and R are as previously defined may be prepared by reacting an aqueous solution of the sodium or potassium salt of N-methyldithiocarbamic acid, N-ethyldithiocarbamic acid, N-propyldithiocarbamic acid, N-butyldithiocarbamic acid, or N-amyldithiocarbamic acid with formaldehyde (conveniently with a 37 percent solution of formaldehyde in water) at a temperature of 25°–35° C. for about thirty minutes. Similarly, compounds having the formula

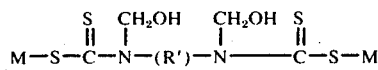

where M and R' are as previously defined may be prepared by reacting with formaldehyde an aqueous solution of the disodium or dipotassium salt of an alkylenebisdithiocarbamic acid containing as the alkylene group one of the following:

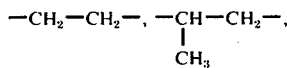

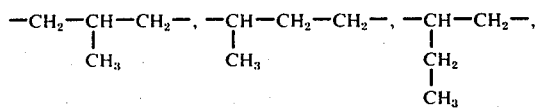

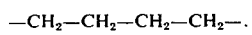

The reaction products obtained as above-described are initially water-soluble, and have good pesticidal activity. However, as previously mentioned, on standing for varying periods of time, precipitates of unknown composition form.

The reaction products obtained as above-described may be stabilized against precipitation by addition of virtually any alkaline material, such as an alkali-metal hydroxide, an amine, ammonia, or an alkaline salt derived from a strong base and a weak acid. We have effectively stabilized the reaction products with sodium hydroxide, potassium hydroxide, sodium sulfite, disodium acid phosphite, sodium acetate, disodium acid phosphate, trisodium phosphate, sodium carbonate, sodium metaborate, sodium thiosulfate, tetrasodium salt of ethylenediaminetetracetic acid, pyridine, ammonia, triethanolamine, tetramethylethylenediamine and monomethylamine. The amount of alkaline material needed is that amount which will stabilize the solution or slurry against precipitation. Preferably, the amount used is that which not only stabilizes the solution but also maximizes the effectiveness thereof. This amount has been determined to be in the range of 0.3 to 0.8 equivalent of alkaline material for each equivalent of dithiocarbamate. In this regard, it will be apparent that twice as much alkaline material is used for each mole of an alkylenebisdithiocarbamate as is used for one of the alkyldithiocarbamates. In one especially preferred embodiment, about 0.5 mole of sodium or potassium hydroxide is used per mole of N-hydroxymethyl-N-methyldithiocarbamate. This amount not only stabilizes the composition but also maximizes effectiveness.

Materials such as monomethylamine are very effective for stabilizing the compositions, and a solution of potassium N-hydroxymethyl-N-methyldithiocarbamate stabilized with monomethylamine has been used commercially with considerable success. However, there are certain disadvantages to the use of monomethylamine and the like. The amine is volatile, and makes accurate formulation somewhat difficult. It has a very strong objectionable odor, and contributes to the formation of N,N'-dimethylthiourea, which is undesirable from an ecological viewpoint.

The compositions of this invention may be prepared in various ways. One general method involves adding formaldehyde (37 percent aqueous solution) to an aqueous solution of an alkali-metal salt of an N-alkyldithiocarbamate on an equimolar basis and reacting at 25°–35° C. for from one-half to two hours, followerd by addition of the alkaline material at 25°–50° C. Similarly, two moles of formaldehyde is used for each mole of N,N'-alkylenebisdithiocarbamate. The above method gives a stabilized aqueous solution of the corresponding N-hydroxymethyl compounds. In some instances, such as when the formaldehyde is added in a more concentrated form or highly concentrated solutions of alkali-metal dithiocarbamate salts are used, the product is in the form of an aqueous slurry. This slurry is likewise stabilized by addition of the alkaline material, thus preventing formation of undesirable precipitates. The slurry form is useful where the product is to be shipped long distances, and can be diluted with water at the point of use to obtain a solution for easier handling.

Specific embodiments of the invention are described in the following examples, which should be considered as exemplary rather than limiting of the invention.

EXAMPLE I

This example describes the preparation of stabilized compositions comprising aqueous solutions of potassium N-hydroxymethyl-N-methyldithiocarbamate. In each case a 55 percent solution of potassium N-methyldithiocarbamate (sometimes referred to as KN-Methyl) in water was reacted with an equimolar amount of formaldehyde. The formaldehyde was added as a 37 percent aqueous solution. The reactants were maintained at 25°–30° C. for one-half hour, and the respective alkaline materials were added to the reaction product at about 30° C. Each of the stabilized compositions was formulated to contain 40 percent potassium N-hydroxymethyl-N-methyldithiocarbamate. The alkaline materials used and the amounts thereof, per mole of dithiocarbamate, were potassium hydroxide (0.50, 0.75, and 1.0 mole), pyridine (1.0 mole), triethanolamine (0.62 mole) and tetramethylethylenediamine (TMEDA, 0.5 mole). The products were tested against *Enterobacter aerogenes* by the pulp substrate method as described in U.S. Pat. No. 2,881,070, and the effectiveness of the stabilized compositions of the invention, as percentage kill after 18 hours, is tabulated in Table 1.

TABLE 1

| pH | Concentration | KN-Methyl | 0.5 mole KOH | 0.75 mole KOH | 1.0 mole KOH | 0.62 mole pyridine | 1.0 mole triethanolamine | 0.5 mole TMEDA |
|---|---|---|---|---|---|---|---|---|
| | Parts per million active ingredient | | | | Percent kill | | | |
| 5.5 | 0.2 | 16 | 12 | 0 | 0 | 96 | 69 | 94 |
| | 0.4 | 0 | 55 | 0 | 7 | 99.95 | 99 | 99.95 |
| | 0.8 | 22 | 100 | 39 | 24 | 99.95 | 100 | 100 |
| | 1.6 | 3 | 99.9 | 99.7 | 99.8 | 99.99 | 99.98 | 99.99 |
| | 3.2 | 41 | 99.98 | 99.95 | 99.97 | 99.99 | 99.99 | 99.99 |
| 6.5 | 0.2 | 25 | 92 | 0 | 17 | 23 | 17 | 18 |
| | 0.4 | 45 | 99.8 | 51 | 30 | 97 | 99 | 99 |
| | 0.8 | 8 | 99.99 | 68 | 46 | 98 | 88 | 98 |
| | 1.6 | 44 | 99.7 | 99.6 | 24 | 97 | 98 | 98 |
| | 3.2 | 73 | 99.99 | 91 | 77 | 97 | 99.8 | 90 |

It is apparent from the above data that the compositions in accordance with the invention were much more effective than a comparable amount of potassium N-methyldithiocarbamate. The compositions stabilized with 0.5, 0.75 and 1.0 mole KOH have been retained for shelf life studies, and have remained as stable solutions for two months. Solutions of potassium N-hydroxymethyl-N-methyldithiocarbamate which were not stabilized with alkaline material began to precipitate within 24 hours.

EXAMPLE II

In this example, aqueous solutions containing 30 percent potassium N-hydroxymethyl-N-methyldithiocarbamate were stabilized with various alkaline materials. Amounts of alkaline material are per mole of dithiocarbamate. The effectiveness of the stabilized compositions against *Enterobacter aerogenes* as determined by the pulp substrate method is shown in Table 2.

TABLE 2

| pH | Concentration | KN-Methyl | Na$_2$SO$_3$ 0.5 mole | Na$_2$HPO$_3$ 0.5 mole | NaOAc 0.5 mole | NaOAc 1.0 mole | HPO$_4$ 0.5 mole | KOH 0.25 mole |
|---|---|---|---|---|---|---|---|---|
| | Parts per million active ingredient | | | | Percent kill | | | |
| 5.5 | 0.2 | 19 | 42 | 86 | 38 | 0 | 0 | 87 |
| | 0.4 | 20 | 30 | 91 | 95 | 93 | 99.6 | 99.9 |
| | 0.8 | 24 | 99 | 99 | 99.8 | 98 | 100 | 99 |
| | 1.6 | 71 | 99 | 99.9 | 99.5 | 99.8 | 99.9 | 100 |
| | 3.2 | 86 | 99.9 | 99.8 | 99.8 | 99.7 | 99.7 | 99.5 |
| 6.5 | 0.2 | 11 | 2 | 36 | 0 | 37 | 39 | 56 |
| | 0.4 | 0 | 34 | 59 | 62 | 36 | 39 | 56 |
| | 0.8 | 45 | 67 | 75 | 59 | 71 | 69 | 24 |
| | 1.6 | 30 | 94 | 93 | 99.7 | 93 | 99 | 96 |
| | 3.2 | 93 | 98 | 99 | 99 | 99 | 99.98 | 69 |

EXAMPLE III

In this example a series of compositions containing 40 percent N-hydroxymethyl-N-methyldithiocarbamate were stabilized with sodium hydroxide in amounts of from 0.4 to 0.8 mole per mole of dithiocarbamate. The stabilized compositions were clear orange solutions, and their effectiveness against *Enterobacter aerogenes* by the pulp substrate method is shown in Table 3, and for comparison purposes a solution of KN-Methyl with 0.5 mole NaOH was also included. As expected, KN-Methyl which had not been reacted with formaldehyde did not perform as well as the compositions of the invention.

TABLE 3

| pH | Concentration | NaOH 0.4 mole | NaOH 0.5 mole | NaOH 0.6 mole | NaOH 0.7 mole | NaOH 0.8 mole | KN-Methyl and NaOH 0.5 mole |
|---|---|---|---|---|---|---|---|
| | Parts per million active | | | | Percent kill | | |

TABLE 3-continued

| | | Alkaline stabilizer added to potassium N-hydroxymethyl-N-methyldithiocarbamate | | | | | KN-Methyl and |
|---|---|---|---|---|---|---|---|
| pH | Concentration | NaOH 0.4 mole | NaOH 0.5 mole | NaOH 0.6 mole | NaOH 0.7 mole | NaOH 0.8 mole | NaOH 0.5 mole |
| | ingredient | | | | | | |
| 5.5 | 0.2 | 0 | 25 | 0 | 0 | 2 | 0 |
| | 0.4 | 55 | 10 | 54 | 22 | 62 | 22 |
| | 0.8 | 99.8 | 99.9 | 99 | 99 | 84 | 0 |
| | 1.6 | 99.7 | 97 | 99 | 99.5 | 99.9 | 0 |
| | 3.2 | 98 | 100 | 99.95 | 99.96 | 99.8 | 37 |
| 6.5 | 0.2 | 86 | 70 | 32 | 31 | 12 | 23 |
| | 0.4 | 99.7 | 99 | 38 | 77 | 89 | 16 |
| | 0.8 | 99.95 | 92 | 99.9 | 99 | 31 | 53 |
| | 1.6 | 99.95 | 97 | 99.8 | 99.9 | 99 | 39 |
| | 3.2 | 99.9 | 94 | 61 | 99.99 | 99 | 43 |

EXAMPLE IV

This example demonstrates the stability of preferred compositions in accordance with the invention, and also shows that the compositions are compatible in the presence of additional materials, specifically with 8 percent sodium 2-mercaptobenzothiazole and 4 percent monoethanolamine. Each of the compositions was an aqueous solution containing 33 percent potassium N-hydroxymethyl-N-methyldithiocarbamate and added materials. The added materials were (1) NaOH (0.5 mole per mole dithiocarbamate), (2) KOH (0.5 mole per mole dithiocarbamate), (3) same as (1) but with 8 percent sodium 2-mercaptobenzothiazole and 4 percent monoethanolamine, and (4) same as (2) but with 8 percent sodium 2-mercaptobenzothiazole and 4 percent monoethanolamine. Each of these compositions was observed for two weeks at 40° C. and −18° C. and no precipitation occurred.

EXAMPLE V

This example illustrates the preparation of a composition in accordance with the invention stabilized with monomethylamine.

A one-liter reaction flask fitted with a mechanical stirrer, condenser, and thermometer was charged with 500 grams (1.96 moles) of an aqueous solution containing 56.8 percent of potassium N-methyldithiocarbamate and reacted at 25° C. with 158.6 grams (1.96 moles) of an aqueous solution containing 37 percent of formaldehyde; the temperature rose to 31°C. Agitation was continued for one hour and then 121.5 grams (1.96 moles) of an aqueous solution containing 50 percent monomethylamine was added over a 30-minute period, maintaining the temperature between 40° and 43° C. with water bath cooling. The solution was agitated for an additional one hour. The product was a clear orange solution.

EXAMPLE VI

This example illustrates the preparation of a composition in accordance with the invention wherein an alkali-metal salt of alkylenebisdithiocarbamate is reacted with formaldehyde and then stabilized with monomethylamine.

An 8-ounce bottle was charged with 50 grams (0.035 mole) of an aqueous solution containing 20 percent potassium ethylenebisdithiocarbamate and was reacted with 5.6 grams (0.069 mole) of an aqueous solution containing 37 percent of formaldehyde. Then 2.2 grams (0.035 mole) of an aqueous solution containing 50 percent monomethylamine was added. The exothermic reaction caused by the addition of the amine was controlled by chilling in ice and the addition of 65.8 grams of water to the reaction mixture. The product was a stable clear orange solution.

Compositions in accordance with the invention are effective against, in addition to *Enterobacter aerogenes*, other organisms including *Desulfovibrio desulfuricans*, *Pseudomonas aeruginosa*, *Aspergillus niger*, *Chaetomium globosum*, and *Penicillium roqueforti*. The compositions have shown good results as nematocides, algicides, and soil fumigants. They have shown preservative properties for many materials, including cutting oils, polyvinyl acetate resins, hydroxyethyl cellulose solutions, and the like. They are very effective generally for controlling the growth and proliferation of pests such as bacteria, fungi, algae and nematodes, and may be used to inhibit microbiological deterioration of organic cellulosic substances, of fresh water or cooling water, of proteinaceous, carbohydrate or synthetic organic polymers used as a component of adhesives, detergents, wax emulsions, floor polishes, inks, cutting fluid emulsions, water-based paints, textile finishes and sizes. They are useful in treating water used in waterflooding operations for recovery of petroleum due to their effectiveness against sulfate-reducing bacteria and slime-forming microorganisms. They are effective also for treating seeds and and living plants. In all of the foregoing, the method of using the compositions comprises adding to or applying the composition in an effective amount to inhibit or control the pests.

The amount required depends on the degree of control desired as well as the particular substrate being treated and the conditions of use. The amount required for effective control in a given environment is readily determinable.

In addition to the compounds used in the foregoing examples, homologous dithiocarbamate compounds as previously defined provide similar results. Also, alkaline materials other than those recited in the examples may be utilized effectively.

We claim:
1. A stable bactericidal and fungicidal composition comprising as the active component thereof a water soluble salt selected from the group consisting of a potassium or a sodium N-hydroxymethyl-N-alkyldithiocarbamate wherein the alkyl group contains from 1 to 5 carbon atoms and a dipotassium or a disodium N,N'-bishydroxymethyl-N,N'-alkylenebisdithiocarbamate wherein the alkylene group contains from 2 to 4 carbon atoms and sufficient water to dissolve said active component plus an alkaline material in an amount sufficient to stabilize the resulting solution.

2. The composition of claim 1 wherein said active component is entirely dissolved in said water.

3. The composition of claim 1 wherein said active component is potassium N-hydroxymethyl-N-methyldithiocarbamate.

4. The composition of claim 1 wherein said active component is disodium N,N'-bishydroxymethyl-N,N'-ethylenebisdithiocarbamate.

5. The composition of claim 1 wherein said alkaline material is selected from the group consisting of sodium hydroxide and potassium hydroxide.

6. The composition of claim 1 wherein said alkaline material is monomethylamine.

7. The composition of claim 5 wherein about 0.5 equivalent of alkaline material is present for each equivalent of said active component.

8. The composition of claim 7 wherein said active component is present in an amount of about 40 percent by weight.

9. The composition of claim 1 wherein about 8 percent sodium 2-mercaptobenzothiazole and about 4 percent monoethanolamine are included.

10. A method of controlling the growth and proliferation of bacteria and fungi which comprises contacting said bacteria and fungi with the composition defined in claim 1 in an amount sufficient to inhibit the growth and proliferation thereof.

11. A method of inhibiting the growth and proliferation of bacteria and fungi in fresh water which comprises adding to said fresh water the composition defined in claim 1 in an amount sufficient to inhibit the growth and proliferation of said bacteria and fungi.

12. A method of inhibiting the growth and proliferation of bacteria and fungi in cooling water which comprises adding to said cooling water the composition defined in claim 1 in an amount sufficient to inhibit the growth and proliferation of said bacteria and fungi.

13. A method of inhibiting the growth and proliferation of bacteria and fungi in an organic substance which is susceptible to microbiological deterioration in the presence of moisture which comprises adding to said organic substance the composition defined in claim 1 in an amount sufficient to inhibit the growth and proliferation of said bacteria and fungi.

14. A method of inhibiting the growth and proliferation of bacteria and fungi on seeds and living plants, which comprises applying to said seeds and living plants the composition defined in claim 1 in an amount sufficient to inhibit the growth and proliferation of said bacteria and fungi.

15. A method of inhibiting the growth and proliferation of bacteria and fungi in soils, which comprises adding to said soils the composition defined in claim 1 in an amount sufficient to inhibit the growth and proliferation of said bacteria and fungi.

* * * * *